US008764792B2

(12) United States Patent
Weiser

(10) Patent No.: US 8,764,792 B2
(45) Date of Patent: Jul. 1, 2014

(54) METHOD AND APPARATUS FOR CLOSING WOUNDS WITHOUT SUTURES

(76) Inventor: Leslie Philipp Weiser, Wellesley, MA (US)

( * ) Notice: Subject to any disclaimer, the term of this patent is extended or adjusted under 35 U.S.C. 154(b) by 1249 days.

(21) Appl. No.: 12/035,048

(22) Filed: Feb. 21, 2008

(65) Prior Publication Data

US 2008/0228220 A1 Sep. 18, 2008

Related U.S. Application Data

(63) Continuation of application No. 10/412,967, filed on Apr. 14, 2003, now abandoned.

(51) Int. Cl.
*A61B 17/08* (2006.01)
(52) U.S. Cl.
USPC ............... 606/213; 606/215; 602/42; 602/54; 602/57; 602/58
(58) Field of Classification Search
USPC ............. 606/213, 215; 602/42, 52, 54, 57, 58
See application file for complete search history.

(56) References Cited

U.S. PATENT DOCUMENTS

| 1,074,413 | A | 9/1913 | DeBaun et al. |
| 1,230,444 | A | 6/1917 | Teed |
| 2,196,296 | A | 4/1940 | Flynn |
| 2,751,909 | A | 6/1956 | Weitzner |
| 3,528,426 | A | 9/1970 | Vukojevic |
| 3,971,384 | A | 7/1976 | Hasson |
| 4,423,731 | A | 1/1984 | Roomi |
| 4,526,173 | A | 7/1985 | Sheehan |
| 4,531,521 | A | 7/1985 | Haverstock |
| 4,655,209 | A | 4/1987 | Scott |
| 4,950,282 | A | 8/1990 | Beisant et al. |
| 5,176,703 | A | 1/1993 | Peterson |
| 5,234,462 | A | 8/1993 | Pavletic |
| 5,263,970 | A | 11/1993 | Preller |
| 5,336,219 | A | 8/1994 | Krantz |
| 5,415,626 | A | 5/1995 | Goodman et al. |
| 5,497,788 | A | 3/1996 | Inman et al. |
| D371,604 | S | 7/1996 | Savage |

(Continued)

FOREIGN PATENT DOCUMENTS

| CA | 2499866 | 1/2006 |
| WO | WO/2006/014323 | 2/2006 |
| WO | 2006040379 A1 | 4/2006 |

OTHER PUBLICATIONS

International Search Report dated Dec. 23, 2005, received in PCT/US05/23362.

(Continued)

*Primary Examiner* — Vy Q Bui
(74) *Attorney, Agent, or Firm* — Burns & Levinson LLP; Jacob N. Erlich; Marlo Schepper Grolnic

(57) ABSTRACT

An elongated flexible base strip is constructed with a bottom surface coated with an adhesive material. The base strip is constructed with bridging links which are spaced along the inner edge of the base strip and extend outward therefrom. The base strip, is cut to a first length and aligned with the wound with the bridging links extending over the wound. A matching portion of base strip is cut to a second length and aligned with the wound with the bridging links opposing. The opposing links are drawn together to close the wound. Adhesive on the links holds the links to the opposite base strip.

10 Claims, 14 Drawing Sheets

(56) References Cited

U.S. PATENT DOCUMENTS

| | | |
|---|---|---|
| 5,534,010 A | 7/1996 | Peterson |
| 5,562,705 A | 10/1996 | Whiteford |
| 5,630,430 A | 5/1997 | Shultz et al. |
| 5,733,308 A | 3/1998 | Daugerty et al. |
| 5,779,659 A | 7/1998 | Allen |
| D401,339 S | 11/1998 | Chambers |
| 5,843,025 A | 12/1998 | Shaari |
| 5,891,077 A | 4/1999 | Gilman et al. |
| 5,947,998 A | 9/1999 | Cartmell et al. |
| 6,007,564 A | 12/1999 | Haverstock |
| 6,043,406 A | 3/2000 | Sessions et al. |
| 6,093,465 A | 7/2000 | Gilchrist et al. |
| 6,176,868 B1 | 1/2001 | Detour |
| 6,293,281 B1 | 9/2001 | Shultz et al. |
| 6,329,564 B1 | 12/2001 | Lebner |
| 6,425,876 B1 | 7/2002 | Frangi et al. |
| 6,468,383 B2 | 10/2002 | Kundel |
| 6,495,230 B1 | 12/2002 | do Canto |
| 6,822,133 B2 | 11/2004 | Lebner |
| 6,831,205 B2 | 12/2004 | Lebner |
| 6,942,683 B2 | 9/2005 | Dunshee |
| 7,022,891 B2 | 4/2006 | Beaudry |
| 7,066,182 B1 | 6/2006 | Dunshee |
| 7,067,710 B1 | 6/2006 | Beaudry |
| 7,074,982 B2 | 7/2006 | Knutson et al. |
| 7,122,712 B2 | 10/2006 | Lutri et al. |
| 7,186,878 B2 | 3/2007 | Beaudry |
| 7,232,454 B2 | 6/2007 | Rousseau |
| 7,267,681 B2 | 9/2007 | Dunshee |
| 7,332,641 B2 | 2/2008 | Lebner et al. |
| 7,354,446 B2 | 4/2008 | Lebner |
| 7,414,168 B2 | 8/2008 | Lebner |
| 7,511,185 B2 | 3/2009 | Lebner |
| 7,696,399 B2 | 4/2010 | Rogers |
| 2002/0099315 A1 | 7/2002 | Lebner |
| 2004/0204740 A1 | 10/2004 | Weiser |
| 2004/0243040 A1 | 12/2004 | Weiser |
| 2005/0020957 A1 | 1/2005 | Lebner |
| 2005/0021081 A1 | 1/2005 | Lebner |
| 2005/0021083 A1 | 1/2005 | Lebner |
| 2006/0142686 A1 | 6/2006 | Morse |
| 2007/0038246 A1 | 2/2007 | Lebner et al. |
| 2007/0038247 A1 | 2/2007 | Lebner et al. |
| 2007/0191752 A1 | 8/2007 | Lebner |
| 2008/0114396 A1 | 5/2008 | Cory et al. |
| 2008/0154168 A1 | 6/2008 | Lutri |
| 2008/0262540 A1 | 10/2008 | Bangera et al. |
| 2009/0240186 A1 | 9/2009 | Fang |

OTHER PUBLICATIONS

Written Opinion of the International Searching Authority dated Dec. 23, 2005, received in PCT/US05/23362.
International Preliminary Report on Patentability dated May 17, 2006, received in PCT/US05/23362.

METHOD AND APPARATUS FOR CLOSING WOUNDS WITHOUT SUTURES

CROSS REFERENCE TO RELATED APPLICATION

This application claims priority as a continuation type application under 35 U.S.C. §120 to U.S. patent application Ser. No. 10/412,967, filed Apr. 14, 2003, currently pending. The aforementioned application is incorporated herein by reference in its entirety.

BACKGROUND OF THE INVENTION

1. Field of the Invention

The disclosure of this application relates to a method and device for closing wounds or incisions without the use of invasive surgical procedures.

2. Background

The most common methods for closing wounds caused by lacerations or surgical incisions are suturing and stapling. Both of these procedures are skin invasive, which can traumatize and compromise the integrity of the wound. They increase the possibility of infection, expose the surgeon, as well as the patient to blood borne disease, leave behind scar tracks and require a follow-up visit for suture or staple removal.

As is well known, a cut that invades deeply into the tissue of the skin generally requires a mechanism for drawing the sides of a wound together to promote healing and to reduce the formation of scar tissue. Surgeons have become skilled in the various techniques of suturing to minimize the resulting blemish that occurs during the healing process. These methods have always generated issues of sterilization and the very nature of suturing requires a threshold of dexterity that escapes many care providers. This is particularly true in emergency situations, which call for immediate treatment to secure the wound for transport or until such time as proper surgery is available. Suturing, even by a skilled surgeon, punctures and stresses skin tissue causing scaring. It is well recognized that a sutureless wound closure would be a great benefit in many situations.

Beginning early in the 20th century, attempts were made to provide non-invasive closures. An early example of this is described in U.S. Pat. No. 1,074,413 (1913), which teaches the use of a pair of strips of fabric having adhesive backing. The strips of fabric are applied in parallel on either side of the wound and are constructed with threads extending transversely to bridge the wound. A compressive force is applied across the wound by tying opposing ends of the transverse threads of adjacent strips. In order to maintain the threads in an orderly fashion prior to use, another strip of fabric is attached to the distal ends of the threads to secure the thread ends in parallel for packaging and applying the closure. In one embodiment the threads are woven into both of the strips and then cut after placement of the strips on either side of the wound.

Another early device is described in U.S. Pat. No. 1,230,444 (1917). This is a woven fabric adhesive element having a gap intermittently formed in the length of the strip. The gap is formed in the weaving process by omitting weft strands (parallel to the length of the strip) in the gap and reducing the number of warp threads (transverse to the length of the strip) in the gap. A limited number of warp threads, therefore, bridge the gap. An advantage of this device is that it may be constructed in continuous lengths and packaged in a roll for convenient storage. A disadvantage is that the ability to apply a cross-wound force would be limited.

A more sophisticated approach is described in the reference Flynn, U.S. Pat. No. 2,196,296 (1940), in which a closure is designed for the express purpose of eliminating suturing. This device illustrates an early step in a trend towards interlocking multiple element devices. Dual adhesive strips are connected to a base adhesive element and to each other by threads woven through eyelets in the base element. The base element is applied to one side of the wound edge and one of the adhesive strips is applied to the other side. A cross wound force can be applied and held by drawing the threads through the eyes and pulling the remaining pair of adhesive strips away from the wound and attaching them to the skin beyond the associated counter part. The construction and assembly of this device is necessarily complex. It employs dual adhesive strips, i.e., the base strip and one of the adhesive strips applied in parallel on either side of the wound, but uses a third adhesive strip to generate and maintain the wound closing force.

U.S. Pat. No. 4,423,731 (1984) describes a suture-less wound closure which is similar to that shown in the above cited '413 patent. In this patent the distal ends of the bridging threads of one adhesive strip are interconnected by a further pulling strip which allows the bridging threads to be manipulated in concert. This configuration requires that the bridging threads or filaments of each of the adhesive strips be interlaced to enable the pulling strips to be pulled across the wound and secured. Dual adhesive strips are constructed with bridging filaments interlaced and attached to a pulling strip also having adhesive. The adhesive strips are applied on either side of the wound and are drawn together by grasping the pulling strips and thereby drawing the edges of the wound together. The closure is secured by adhering the pulling strip to the skin on the outer side of the opposing adhesive strip. Opposing forces can be applied simultaneously to each of the adhesive strips at the wound edge to close the wound.

The suture-less closure of U.S. Pat. No. 5,263,970 (1993) operates similarly to the closure of the '731 patent. It is however, formed of a single adhesive element which is placed over the wound. Centrally located over the wound opening, there are constructed dual sets of separated elongated extensions. The distal ends of each set of extensions are attached by a laterally extending tab portion. By manipulating the tabs, each set of extensions may be independently manipulated to allow the wound edges to be pulled together or otherwise advantageously moved. The closure is secured by adhering the tabs to adhesive pads on the exposed surface of the adhesive element.

An interlocked assembly of adhesive pads are assembled in the system of U.S. Pat. No. 5,534,010 (1996) to be operated in a manner similar to the '731 patent discussed above. First and second pads are adapted for application to the skin on either side of the wound. A third and fourth pad are adapted to adhere to the upper side of the first and second pads respectively. The third pad is attached by bridging filaments to the first pad and may be applied to the upper side of the second pad and the fourth pad is attached by bridging filaments to the second pad and may be applied to the upper side of the first pad.

In the bandage of U.S. Pat. No. 6,329,564 (2001), a two component interlocked system is devised which operates similarly to the system of the '010 patent. First and second adhesive strips are constructed with elongated connectors extending transverse to bridge the wound. The connectors are in turn interconnected by a pulling element. The adhesive strips, connectors, and pulling elements are interlaced so the connectors of one adhesive strip extend over the outer surface of the opposing adhesive strip. Similarly to the assembly discussed above opposing forces maybe applied to draw each of the adhesive strips toward each other and thereby close the wound.

All of the above bandage configurations, in particular the interlocked dual element style, appear to be difficult to manufacture and to use. The manipulation of a loose assembly of multiple parts in an emergency and possibly life-threatening situation is a challenging undertaking. It is a purpose of this invention to provide a suture-less wound closure which is more easily manufactured and packaged. It is another purpose of this invention to provide a wound closure which is easy to unpackage and apply.

The above cited prior art is consistent in several respects, namely, that two adhesive strips need to be provided for application to either side of the wound and that a mechanism is needed to apply forces to each of the adhesive strips to draw them together to close the wound. The prior art seems to solve this need by proposing multiple interlaced parts.

It is a purpose of this invention to construct a suture-less wound closing device in one piece that can be used on both sides of a wound without the need for interlacing the parts during manufacture. It is a purpose of this invention to provide a single element wound closure that does not require suturing, stapling or gluing.

A simple one piece closure is historically represented by the STERI-STRIP® adhesive strip available from 3M Corporation or butterfly shaped adhesive strips both of which are used to bridge the wound. These configurations may be used singly, in pairs, or multiple units to apply a closing force to the wound. A more complex version of such wound closures is shown in U.S. Patent Application, Pub. No. 2002/0099315, which was published Jul. 25, 2002. A substantially more complex version of this type of closure is described in U.S. Pat. No. 6,293,281 (2001).

A purpose of this invention is to simplify, improve upon, and facilitate the customization capability of these various adhesive strips, wound closure devices and methods. A purpose is to provide a simplified elemental device capable of applying a series of adhesive bandage strips that can be used to close wounds and can be adapted to a variety of surgical needs, incision sizes, and types of wounds. It is a further purpose of this invention to provide a closure that does not require any particular dexterity, skill, or knowledge and is reasonable in cost so that it can be used by anyone.

In the course of describing this invention below, the bottom of the closing device of this invention will refer to the surface that is intended to engage the skin and the upper side or top will refer to the side of a component that is facing away from the skin after application. Directions will be indicated according to the position of the wound being treated, for example, transverse shall refer to directions across the wound. The inner edge of the closing device shall refer to the side which is intended to be adjacent to the wound lip and the outer edge shall refer to the side of the device that is intended to be away from the wound.

SUMMARY OF THE INVENTION

The main element of this invention comprises an elongated flexible base strip having its bottom surface coated with an adhesive material suitable for adherence to skin. The base strip is constructed with bridging links which are spaced along the inner edge of the base strip and extend outward therefrom. The inner edge of the base strip, from which the links extend, is intended to be aligned with a lip of the wound being treated. Each of the bridging links has an adhesive coated section displaced from the inner edge. In the packaged or stored position, prior to engagement, the bridging links are folded over the upper surface of the adhesive strip about a hinge that is at the joint of the bridging link to the base strip. The base strip may be of an extended length so that it might be customized to size and shape of the wound.

In order to package the closure device of this invention, protective tapes may be positioned over exposed adhesive material to preserve the adhesive characteristics and avoid undesirable sticking to packaging materials surgical gloves, and other non-designated areas surrounding the wound. To facilitate positioning of the closure device, the protective tape covering the bottom surface may be constructed to expose a region of the adhesive which is immediately adjacent to the inner edge. This inner edge region of adhesive permits the practitioner to apply the base strip without fully engaging the entire adhesive area. The inner edge of the base strip may then be adjusted into alignment with the edge of the wound. After alignment with the wound, the remaining protective tape is removed and the entire base strip is secured adjacent to the wound.

In the stored position the adhesive sections of the bridging links will be exposed on the top surface of the links. A protective tape is applied to cover these adhesive sections.

In operation the wound will be examined and two substantially equal lengths of the base strip will be cut, torn, or separated from the packaged closure device. In many instances, the contour of the wound will need to be manipulated to form a substantially straight lip to facilitate alignment of the inner edge of the base strip. The inner edge of each length of the base strip is positioned on opposite sides of the wound. The base strip is adjusted to insure that the bridging links on one side of the wound are displaced from the bridging links on the other. To close the wound the bridging links are manually pivoted about a hinge from their stored position and pulled transverse to the wound lip to close the wound. The closing force is maintained by engaging the adhesive section of the bridging links to the upper surface of the opposite length of base strip across the wound.

BRIEF DESCRIPTION OF THE DRAWINGS

The invention will be described in more detail below with reference to the attached drawings in which.

DETAILED DESCRIPTION OF THE PREFERRED EMBODIMENTS

The invention of this application involves a single component wound closure which is easy to manufacture and simple to use. It is useable to reliably close a wide variety of wound openings, large and small. It is designed for ease of use in any environment, whether it is a field emergency or an in hospital surgical procedure. It employs the basic concept of providing a single component surgical strip which can be used on both sides of the wound and avoids the difficulties of complex interlaced multiple component bandages.

Figure 1:
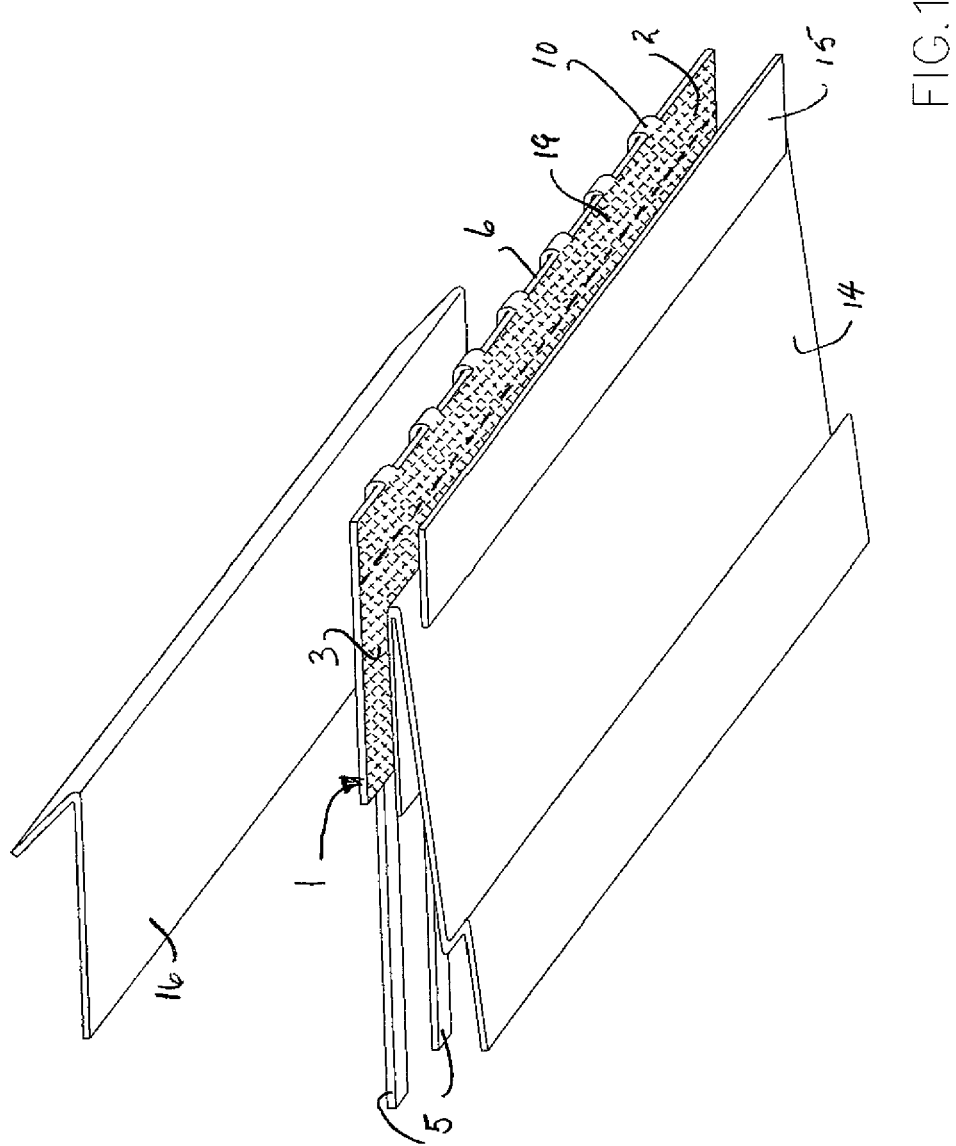
FIG. 1 is a perspective view of a closure device of this invention from the bottom with a first embodiment of protective tapes exploded.
Figure 2:
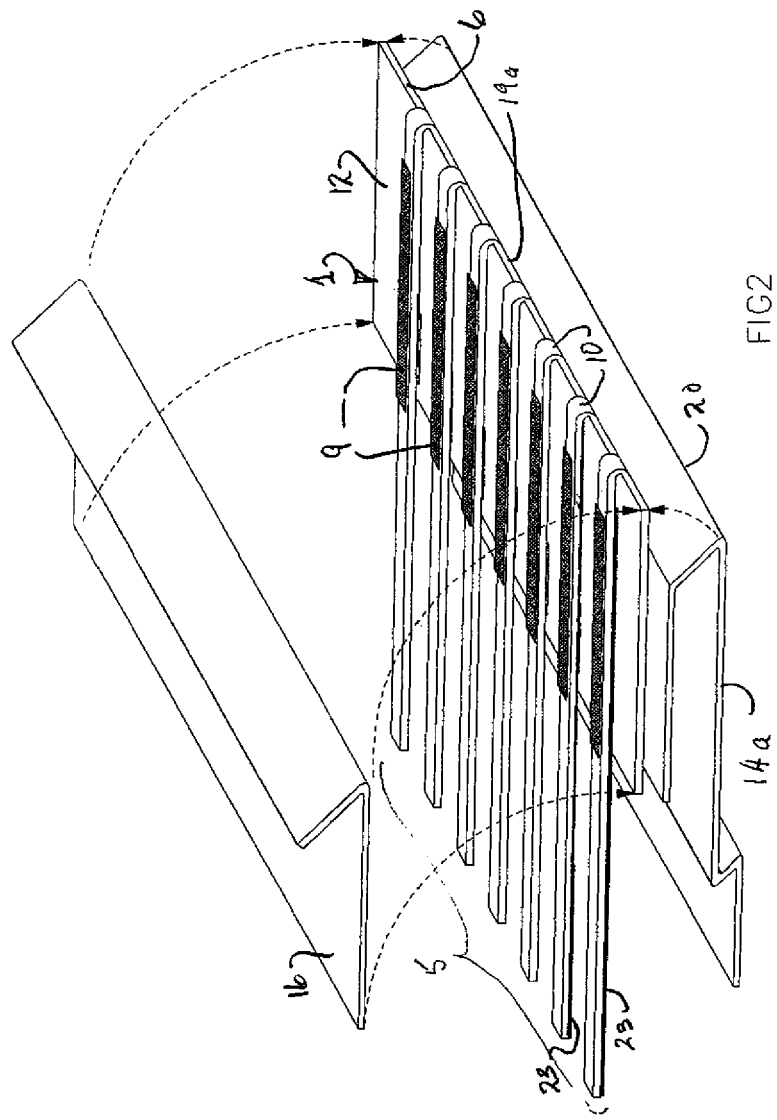
FIG. 2 is a perspective view of a closure device of this invention from the top, with a second embodiment of protective tapes exploded.
Figure 3:
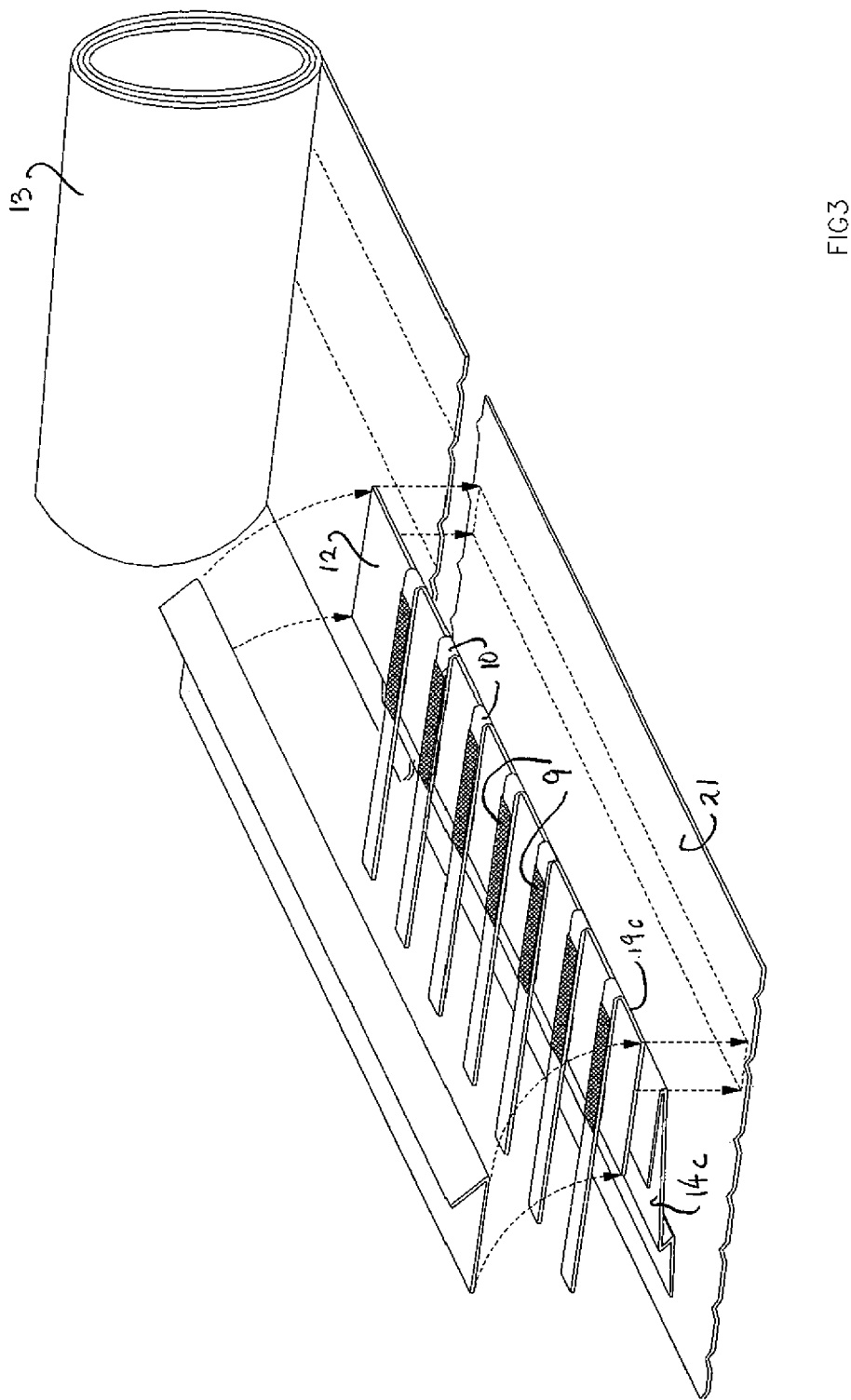
FIG. 3 is a perspective view of a closure device of this invention from the top, with a third embodiment of protective tapes exploded.
Figure 4:
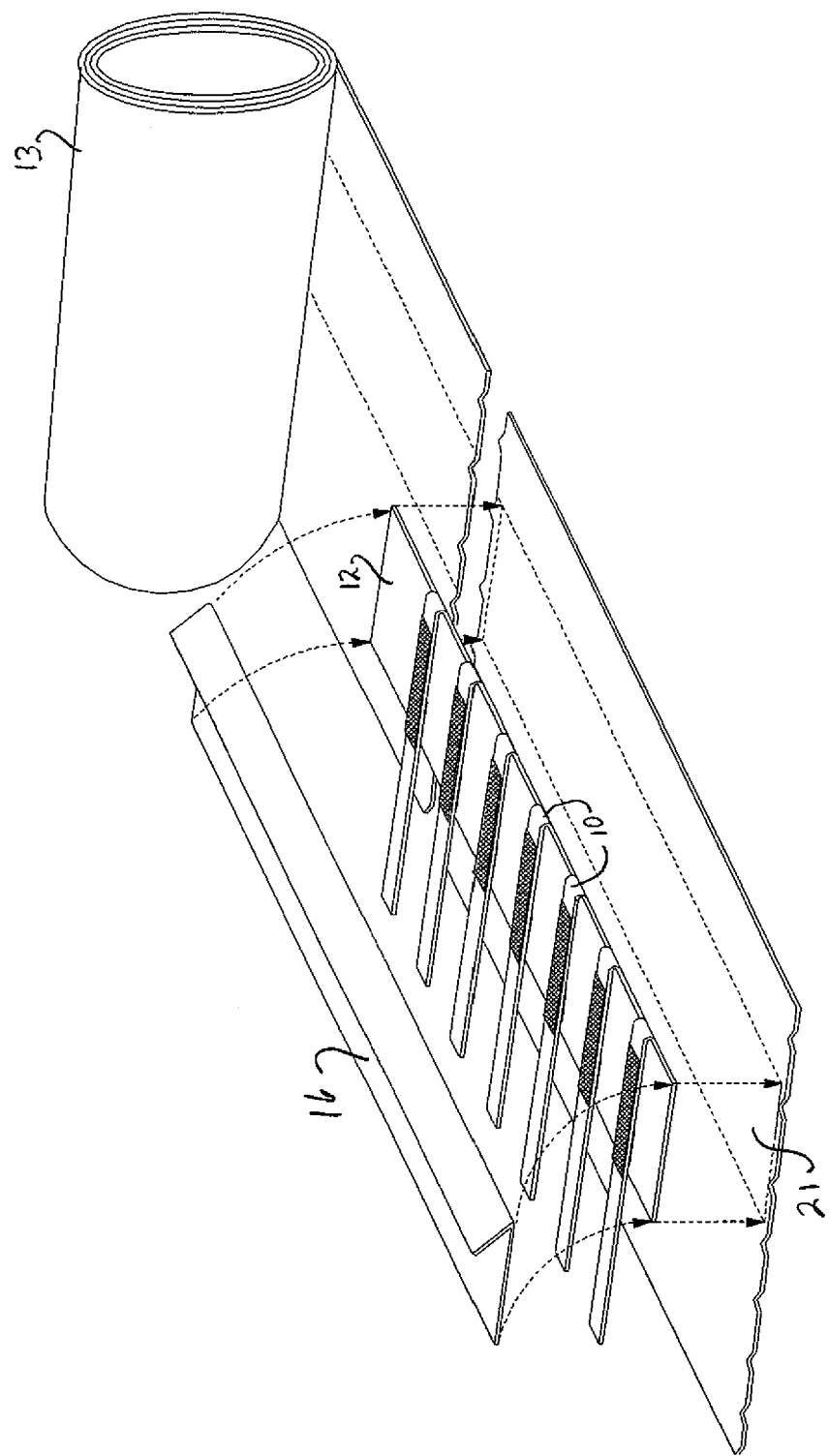
FIG. 4 is a perspective view of a closure device of this invention from the top, with a forth embodiment of protective tapes exploded.
Figure 5:
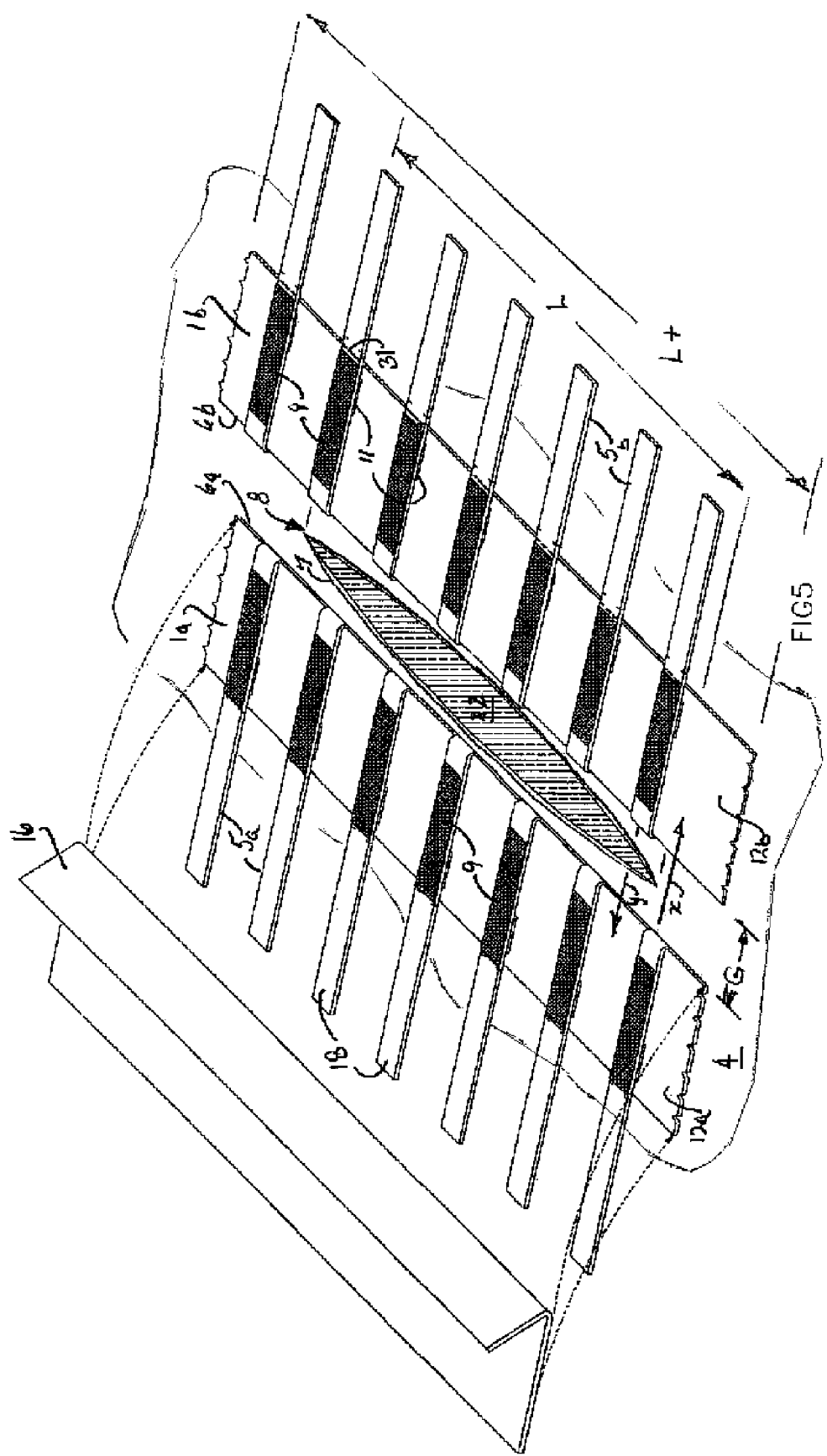
FIG. 5 is a perspective view of a closure device of this invention from the top, with aligned lengths of base strips applied to a wound.

As shown in FIGS. 1-8, an elongated flexible base strip 1 forms the main element of this invention and is constructed having its bottom surface 2 coated with an adhesive material 3 suitable for adherence to skin 4 (FIG. 5). As shown in FIG. 2, base strip 1 is constructed with multiple bridging links 5 that extend generally transverse to the base strip 1. The links 5 are spaced along the inner edge 6 of the base strip 1 and extend outward therefrom. The inner edge 6 of the base strip 1, from which the links 5 extend, is intended to be aligned with a lip 7 of the wound 8 being treated, as shown in FIG. 5. Each of the bridging links 5 has an adhesive coated section 9, on its bottom (engaging) surface 18, displaced from the inner edge 6.

Figure 11:
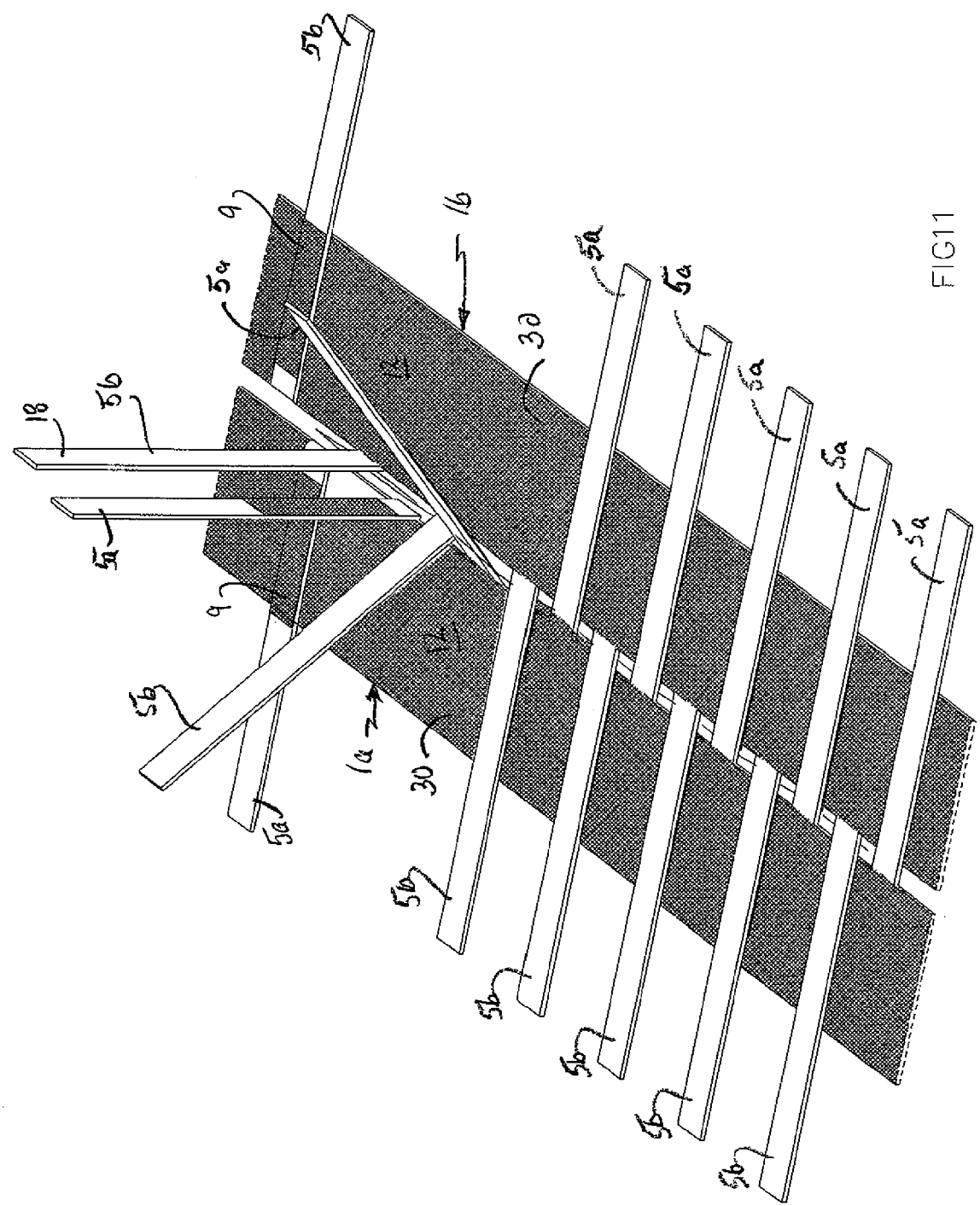
FIG. 11 is a perspective view of an alternate embodiment of the invention with the engaging adhesive section resident on both the base strip and the bridging links.
Figure 13:
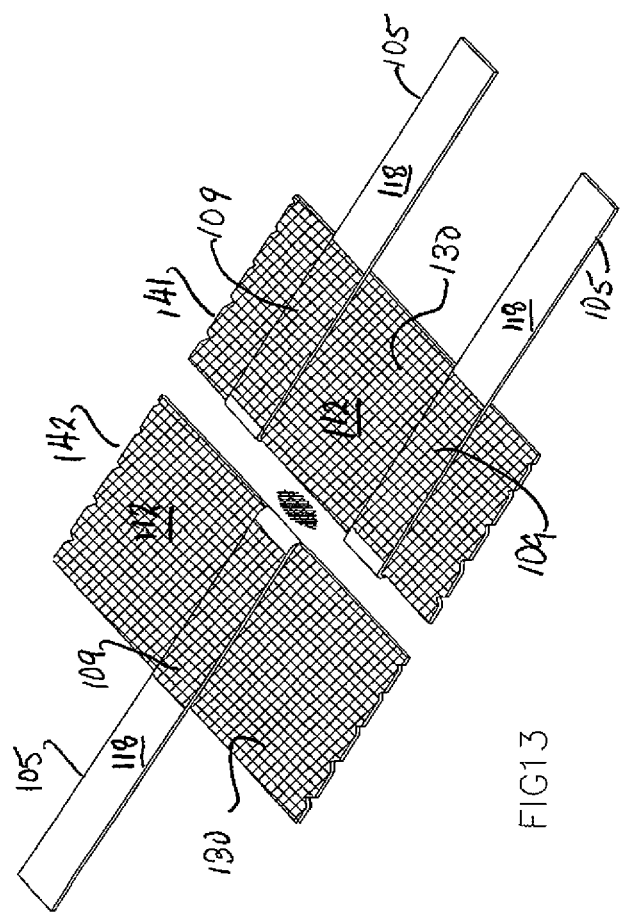
FIG. 13 is a perspective view of the embodiment of FIGS. 9 and 10 with the engaging adhesive resident on both the base strip and the bridging links.

In an alternative embodiment, as shown in FIGS. 11 and 13, an additional adhesive coated section 30 (130 in FIG. 13) is coated on both the top surface 12 of the base strip 1 (112 in FIG. 13) and the engaging surface 18 (118 in FIG. 13) of the bridging links 5 (105 in FIG. 13).

Figure 12:
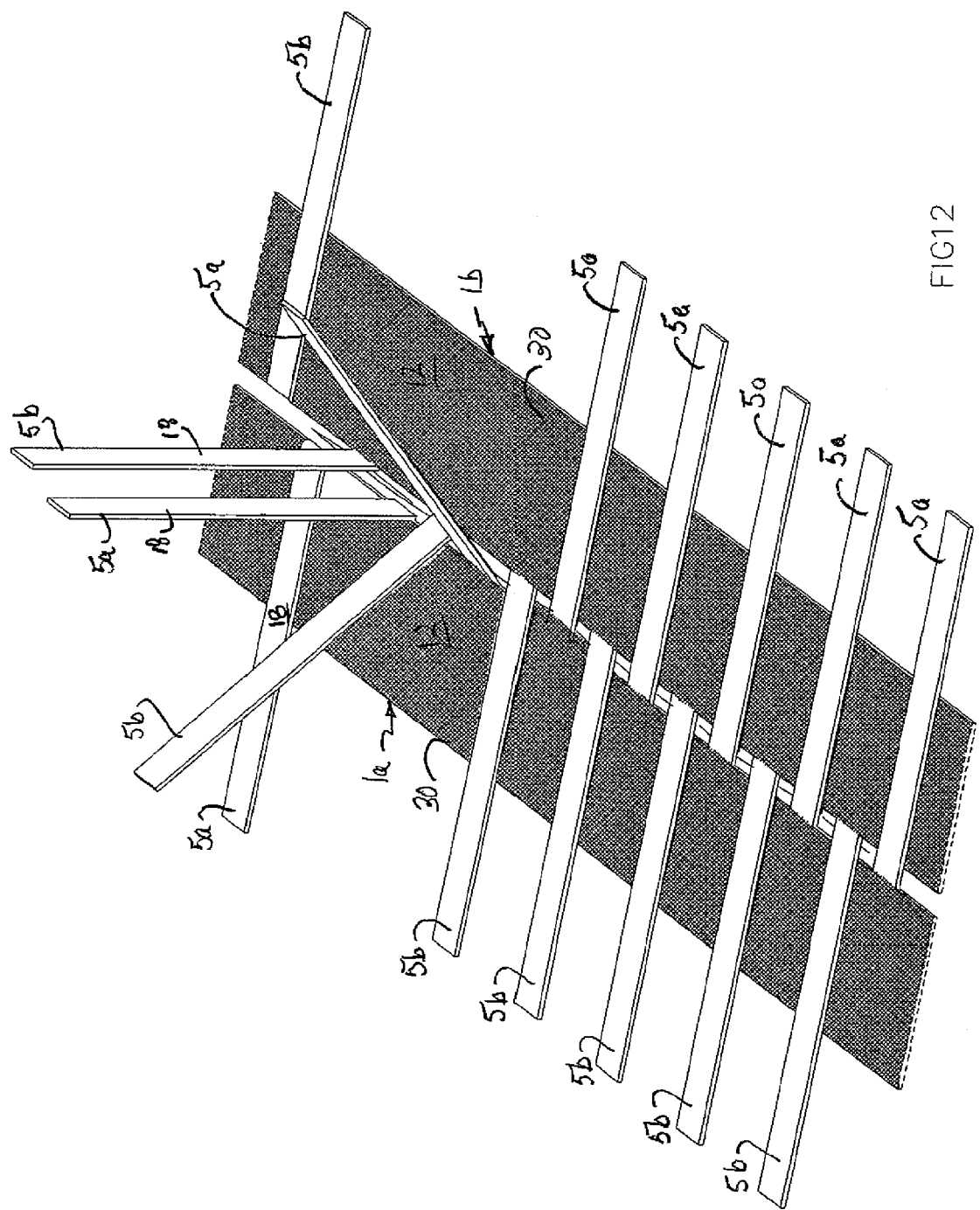
FIG. 12 is a perspective view of an alternate embodiment of the invention with the adhesive section for engaging the bridging links only resident on the base strip.
Figure 14:
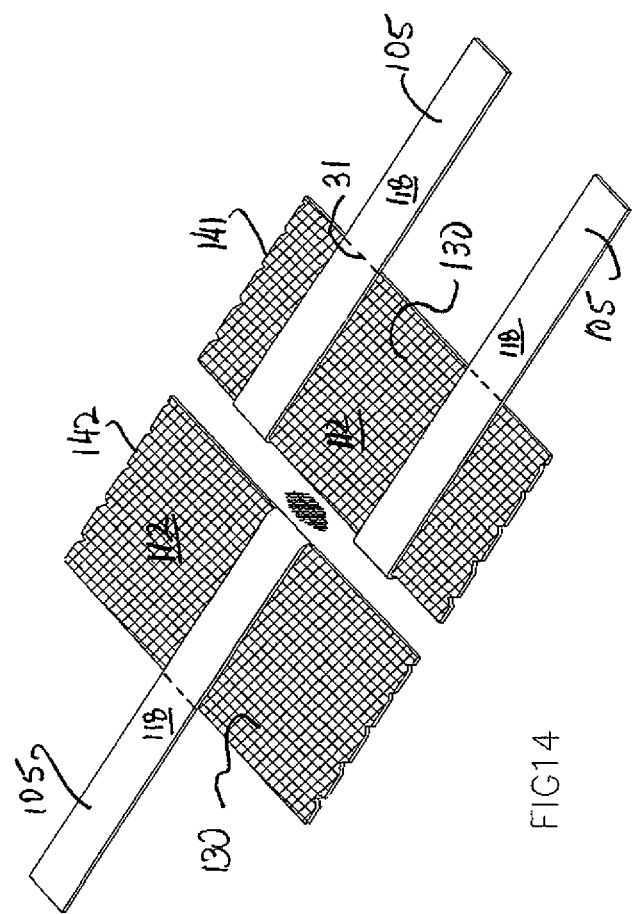
FIG. 14 is a perspective view of the embodiment of FIGS. 9 and 10 with the engaging adhesive on the base strip only.

In another alternative embodiment, as shown in FIGS. 12 and 14, the adhesive coated section 9 is absent from bridging links 5 and an adhesive section 30 (130 in FIG. 14) is applied to top surface 12 (112 in FIG. 14) of base strip 1. Adhesive sections 30 (130) receive the engaging surface 18 (118 in FIG. 14) of each bridging link 5 (105) and hold the links 5 (105) securely in their bridging position.

The base strip 1 and its associated bridging links 5 may be constructed by stamping from a single elongated sheet of plastic material. Alternatively molding or extruding processes may be advantageously used. In some circumstances, it may be advantageous to stiffen the bridging links to facilitate handling. The bridging links may be made more rigid by laying up a second or third layer of plastic sheet material or by otherwise thickening the plastic material in the area of the bridging links 5, as shown in FIG. 2.

In the packaged or stored position, as shown in FIGS. 1 and 2, the bridging links 5 are folded over the upper surface 12 of the adhesive base strip 1 about a hinge 10 that is at the joint of the bridging links and base strip 1. Hinge 10 may be a hinge region formed to provide increased flexibility where bridging links 5 are joined to the base strip. As shown, no adhesive is applied to the hinge region.

Figure 6:
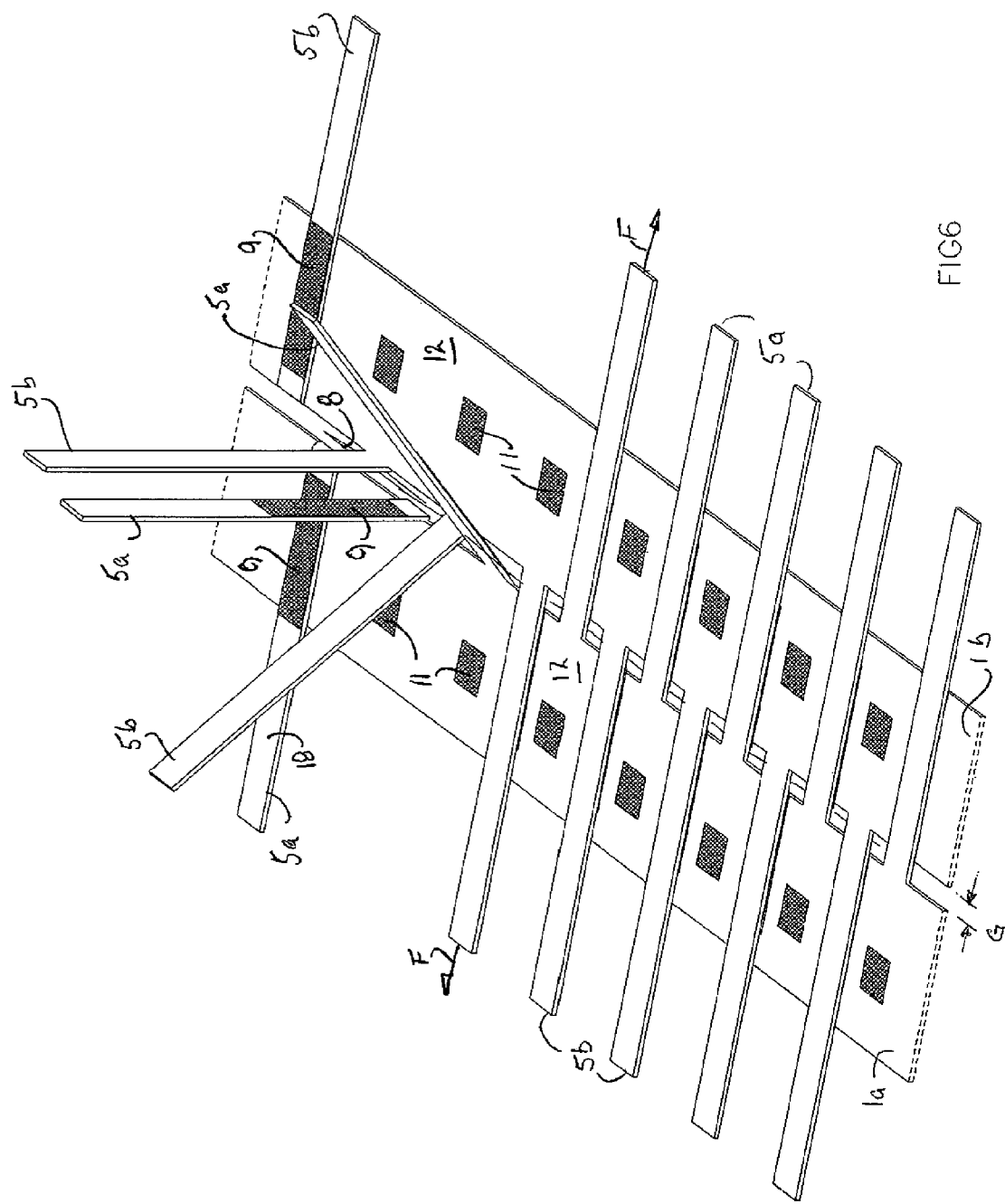
FIG. 6 is a perspective view of a closure device of this invention from the top, with some of the bridging links engaged.

As shown in FIG. 6, a small amount of adhesive 11 can be used on the upper surface 12 of the base strip 1 to engage each of the folded bridging links 5 and releasably hold them in a stored position, see FIGS. 1-4. The base strip 1 may be of an extended length so that it might be cut, torn, or otherwise separated to the desired size, depending on the wound. It could also be packaged in a rolled configuration 13 as shown in FIGS. 3 and 4 and separated as needed.

Folding the bridging links 5 provides an uncluttered operating edge with which to properly align base strip 1 with the wound lip 7.

In order to package the closure device of this invention, protective tapes, such as 14, 15, and 16 shown in FIG. 1, may be positioned over exposed adhesive materials 3 and 9. Protective tapes 14, 15 and 16 act to preserve the adhesive characteristics while helping to avoid undesirable, sticking to packaging materials and other areas surrounding the wound.

To facilitate positioning of the closure device, protective tape covering the bottom surface 3 may be constructed in two parts a main part 14 and an edge part 15. The edge part 15 of the protective tape is aligned with the inner edge 6 of the base strip 1 and is of limited width. This allows the initial exposure of a limited edge adhesive surface 19. This in turn allows the base strip 1 to be aligned with the wound 8 and adjusted prior to adhering the entire base strip 1 adjacent to the wound 8.

In the stored position, the adhesive sections 9 of the bridging links 5 will be exposed as shown in FIGS. 1-4. A protective tape 16 is applied to cover the adhesive sections 9. To assist the user in applying the closure, each of the tape elements may be color coded or otherwise identified to indicate the order of removal. For example: in the removal of the parts 14 and 15 of the bottom protective tape, and the top protective tape 16, different colors or transparency tints may be used. Alternatively, the parts may be numbered or otherwise labeled to indicate the order of removal.

In an alternative embodiment, as shown in FIG. 2, the protective tape 14a is formed in one piece having a fold or perforated line 20 constructed a distance outward from the inner edge 6 and extending the length of the edge 6. By partially removing the tape 14a up to the fold line 20, the limited edge adhesive 19a may be exposed to accomplish the same purpose as indicated above.

In another alternative embodiment, as shown in FIG. 3, edge adhesive 19c is defined by limiting the width of tape 14c to leave the edge adhesive 19c exposed. The edge adhesive is covered in this embodiment only by the exterior packaging sheet 21. In the further alternative embodiment of this invention, as shown in FIG. 4, the protective tapes 14 and 15 are eliminated and the exterior packaging sheet 21 provides the necessary protection from exposure.

To complete the packaging of the closure device of this invention, a tear away outer package, constructed of appropriate sheet material 21 is used to provide an overall sterile wrap for the closure, as is well known. In some situations wrap 21 can be used to protect exposed adhesive sections, if no protective tapes are used. An overall wrap 21 surrounds the closure device and is edge sealed to maintain sterile conditions. When packaged in an extended length such as a roll, a variety of lengths of base strip 1 may be precut and contained in sealed segments of wrap 21 or means may be provided to create an edge seal at the cut edge of a packaged closure which is of continuous length.

A typical wound 8 caused by a laceration or surgical incision is shown in FIG. 5 having a lip 7 at the edge of the gap 22. Before the closure of this invention is applied, the wound 8 is examined to determine the length L of wound 8. The base strip is then cut to a length L+ which is slightly longer than wound 8. Two approximately equal lengths 1a and 1b of the base strip 1 are cut, torn or otherwise separated from the packaged closure device, as for example roll 13. After removing the outer wrap 21, edge protective tape 15 is removed to expose adhesive edge 19. In many instances the wound lip 7 will be curvilinear or otherwise of irregular shape because of natural skin tension or the nature of the injury. This may require manipulation of the skin surrounding the wound to bring the lip 7 into a substantially straight form to accommodate the straight edge 6 of base strip 1.

The inner edges 6a and 6b of each length of the base strips 1a and 1b are positioned adjacent the lip 7 of the wound 8. Base strips 1a and 1b are adjusted to insure that the bridging links 5a on one side of the wound 8 are displaced from the bridging links 5b on the other side, as shown by arrows x and y in FIG. 5. At this point the remaining part 14 of protective tape is removed and the base strips 1a and 1b are secured to the skin in place adjacent to the wound. Protective tape 16 may then be removed to expose adhesive sections 9.

As shown in FIGS. 5 and 6, to close the gap 22 of wound 8, the bridging links 5a and 5b are manually pivoted from their stored position and pulled transverse to the wound lip 7.

Figure 7:
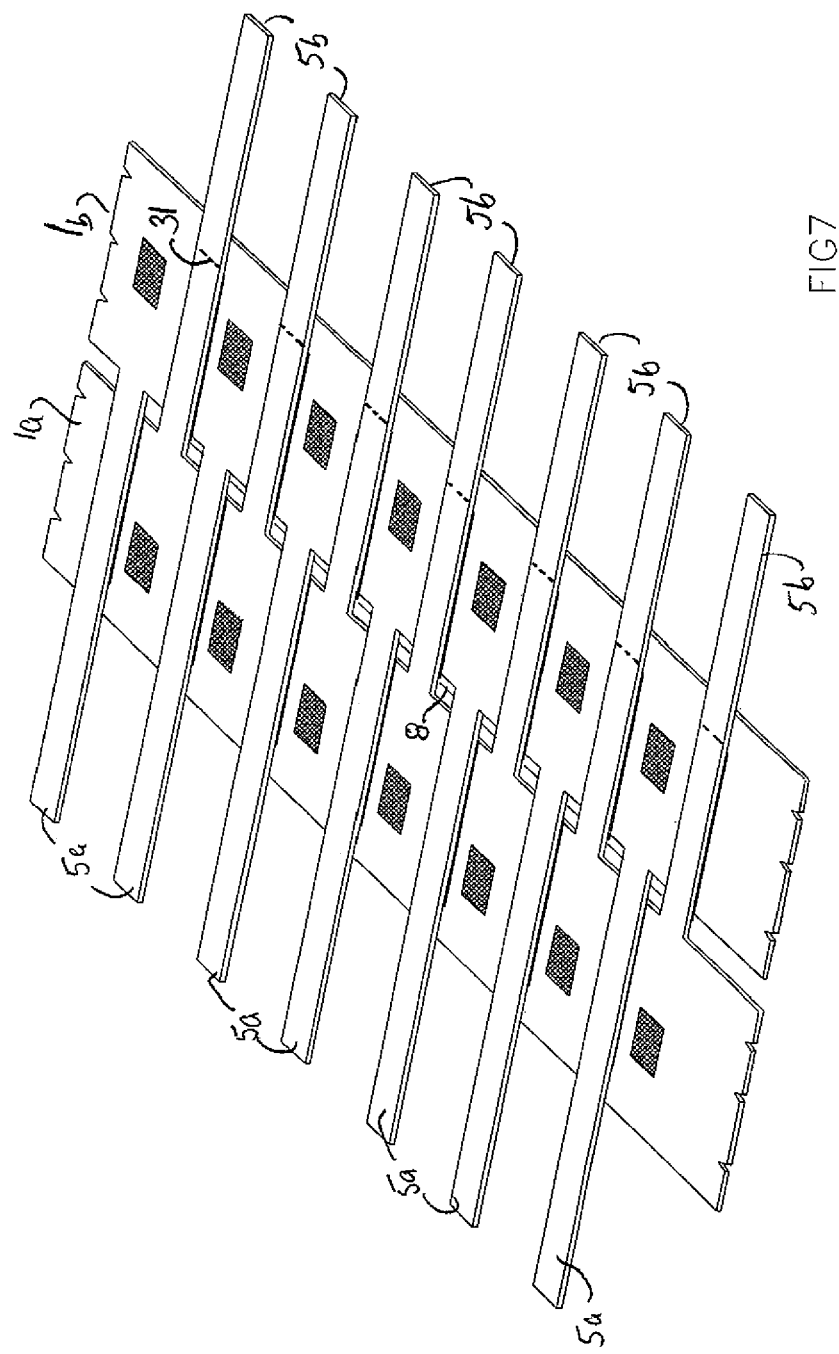
FIG. 7 is a perspective view of a closure device of this invention from the top, in the completely engaged condition.

By simultaneously exerting a force F on pairs of adjacent bridging links 5a and 5b from opposing sides of the wound, the base strips 1a and 1b and the wound lip 7 will be drawn together to close gap 22, as shown in FIG. 6. The space G between the inner edges 6a and 6b of the lengths 1a and 1b, shown in FIGS. 5 and 6, is reduced during this process. It is advantageous to adjust the position of the operating edges 6 so that a small separation G' remains after the wound is closed. This will leave room for the emission of exudates from the wound, while also providing access for the delivery of medication. The closing force is maintained by engaging the adhesive section 9 of the bridging links 5a and 5b to the upper surface 12 of the opposite length of base strip 1 across the wound 8. The bridging links 5a and 5b are thus applied until the wound is closed and secure, as shown in FIG. 7. To provide an uncluttered overall wound dressing, the excess portions of bridging links 5 may be trimmed by cutting or tearing along perforations 31 which may be constructed in each link.

In this manner a simple closure is constructed which is easier to manufacture and use than the multiple component devices of the prior art.

Figure 8:
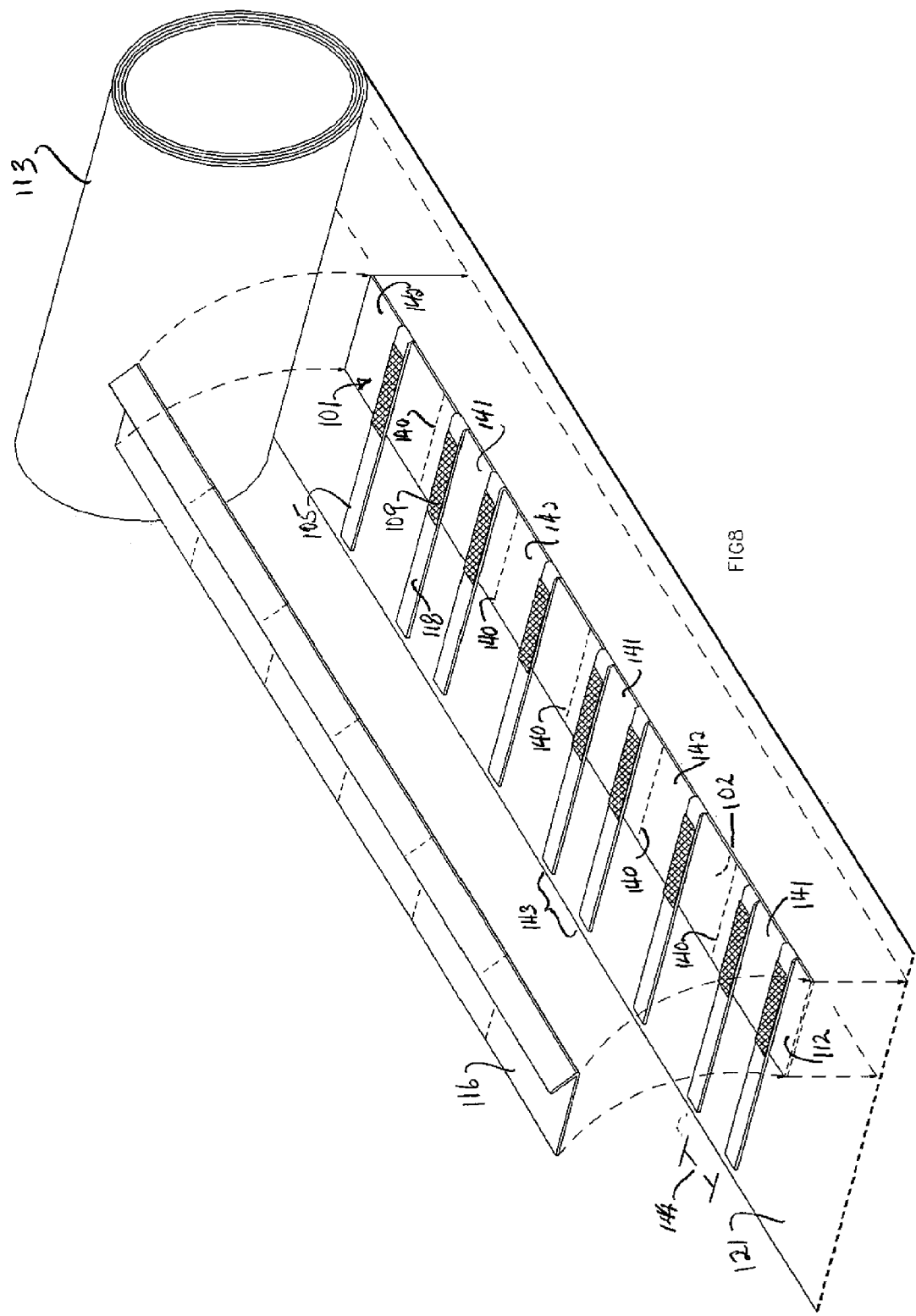
FIG. 8 is a perspective view of an alternate embodiment of the closure device of this invention from the top.
Figure 9:
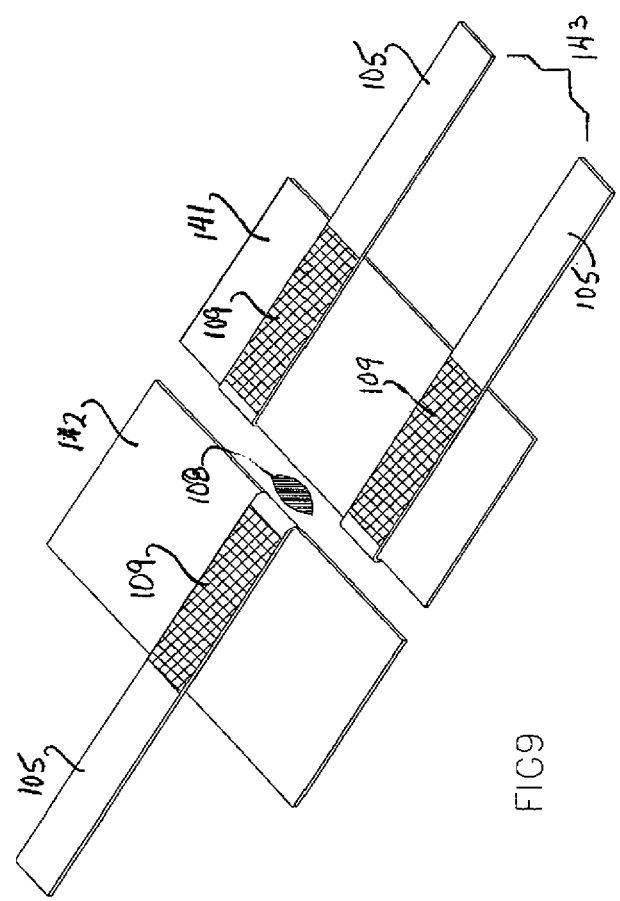
FIG. 9 is a perspective view of an alternate embodiment of the closure device of this invention from the top with aligned lengths of the base strip applied to the wound.
Figure 10:
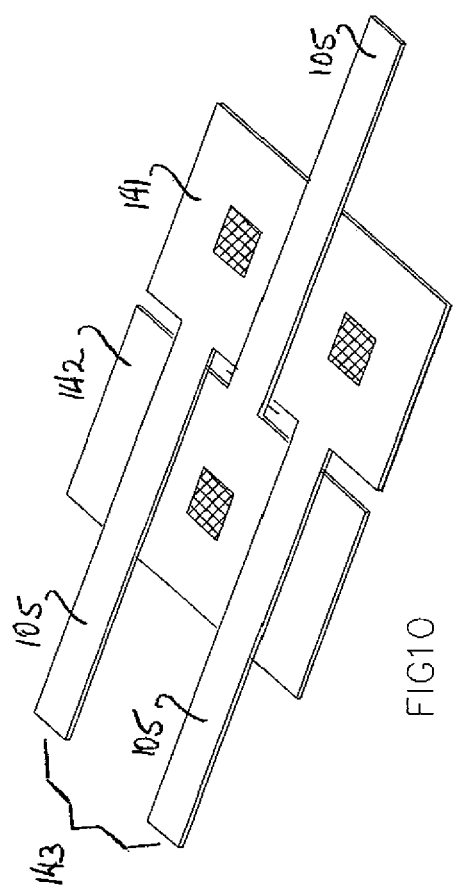
FIG. 10 is a perspective view of an alternate embodiment of the closure device of this invention from the top in a fully engaged condition.

To facilitate the closure of small wounds or partial areas of larger wounds, the adhesive strip may, in the alternative, be constructed as shown in FIGS. 8-10. In this embodiment the components are arranged generally as described before. An elongated adhesive base strip 101 is formed having multiple bridging links 105. The bottom 102 is coated with an adhesive material. Adhesive sections 109 are applied to the top surface 118 of bridging link 105. The base strip 101 may be sealed in sterile packages of various lengths, in rolled configurations 113, or other appropriate means.

To facilitate use of the strips in short units, the bridging links 105 are spaced differently. The base strip 101 is divided, by markings and/or perforated lines 140, into operational units 141 and 142. The units 141 and 142 are marked off over the entire length of base strip 101. A pair 143 of links 105 is positioned together with a normal spacing 144 within the first unit 141. The pair 143 is centered within the unit 141. A single link 105 is then positioned in the center of the adjacent unit 142. This arrangement is alternated over the length of the base strip 101. To use this alternative embodiment, the base strip 101 is cut or separated to obtain one operational unit 141, having a pair 143 of bridging links 105, and one operational unit 142, having a single bridging link 105. Operational units 141 and 142 are placed on opposite sides of wound 108, as shown in FIG. 9. By aligning the units 141 and 142, the bridging links 105 can be applied without interference, as shown in the secured closure in FIG. 9.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

I claim:

1. A method for closing an open wound of predetermined length using a device comprised of a base having adhesive thereon and an edge, a plurality of spaced apart bridging links extending from said edge having adhesive on a portion thereof with tips thereof being substantially free from adhesive, and adhesive-free flexible means for linking the bridging links to the base, the method comprising:
    selecting a slightly longer length than said predetermined length of the wound for the length of the base of the device having a set of spaced apart bridging links;
    applying initially the edge of said slightly longer predetermined length of said base of the device onto a surface on one side of the wound, adjacent to a lip of the wound and substantially parallel to said lip of the wound while adhering the edge of said base to said surface, bringing said lip into substantially straight form and leaving a small distance between said edge of the base and said lip of the wound;
    unfolding the spaced apart bridging links from their storage position in which the bridging links are folded back over said base;
    applying the spaced apart bridging links across the opening of the wound to an opposite side of the wound;
    adjusting the positions of the spaced apart bridging links in order to close the wound, substantially having the opening of the wound crossed by said adhesive-free flexible means only, so that a small separation remains after the wound is closed; and
    adhering said spaced apart bridging links to a surface on the opposite side of the wound.

2. The method of claim 1 further comprising removing any protective means for covering said base of the device.

3. The method of claim 1 further comprising holding at least one tip of said bridging links to facilitate positioning of said bridging links.

4. The method of claim 1 further comprising holding at least one tip of said bridging links to facilitate releasing and repositioning of said bridging links after said adhering step.

5. A method for closing an open wound of predetermined length using a device comprised of a base having adhesive thereon and an edge, a plurality of spaced apart bridging links extending from said edge having adhesive on a portion thereof with tips thereof being substantially free from adhesive, and adhesive-free flexible means for linking the bridging links to the base, the method comprising:
    separating said base of the device into at least a first and a second lengths, said at least first and second lengths having first and second sets of spaced apart bridging links, respectively;

selecting a slightly longer length than said predetermined length of the wound for at least said first of said lengths of the base of the device having bridging links;

applying initially the edge of said first length of said base onto a surface on one side of the wound, adjacent to a lip of the wound and substantially parallel to said lip of the wound, while adhering said base to the surface, bringing said lip into substantially straight form and leaving a small distance between said edge of the base and said lip of the wound;

applying initially the edge of said second length of said base onto a surface on one side of the wound, adjacent to a lip of the wound and substantially parallel to said lip of the wound, while adhering said base to the surface, bringing said lip into substantially straight form and leaving a small distance between said edge of the base and said lip of the wound;

unfolding said spaced apart bridging links from their storage position in which they are folded back over said base;

applying said spaced apart bridging links across the opening of the wound while directing successive spaced apart bridging links from said first set into spaces between successive spaced apart bridging links from said second set;

adjusting the positions of said spaced apart bridging links as to close the wound, substantially having the opening of the wound crossed by said adhesive-free flexible means only, so that a small separation remains after the wound is closed; and adhering said first set of spaced apart bridging links to said second length of said base and said second set of spaced apart bridging links to said first length of said base.

6. The method of claim 5 further comprising removing any protective means for covering said base of the device.

7. The method of claim 5 further comprising removing any protective means for covering said bridging links.

8. The method of claim 7 further comprising guiding the method by utilizing any user guiding means visible on any base covering protective means and any bridging links covering protective means.

9. The method of claim 5 further comprising holding at least one tip of said bridging links to facilitate positioning of said bridging links.

10. The method of claim 5 further comprising holding at least one tip of said bridging links to facilitate releasing and repositioning of said bridging links after said adhering step.

* * * * *